United States Patent
Gittleman

(10) Patent No.: US 10,258,434 B1
(45) Date of Patent: Apr. 16, 2019

(54) CIP FOR SCANNED AND EMBEDDED LOW PROFILE SNAP-IN WINGED DUAL USE DENTAL IMPRESSION POST

(71) Applicant: EVOLLUTION IP HOLDINGS INC., Wilmington, DE (US)

(72) Inventor: Neal B. Gittleman, Houston, TX (US)

(73) Assignee: Evollution IP Holding, Inc., Wilmington, DE (US)

( * ) Notice: Subject to any disclaimer, the term of this patent is extended or adjusted under 35 U.S.C. 154(b) by 0 days.

(21) Appl. No.: 15/812,611

(22) Filed: Nov. 14, 2017

Related U.S. Application Data

(63) Continuation-in-part of application No. 15/594,629, filed on May 14, 2017.

(51) Int. Cl.
*A61C 8/00* (2006.01)
*A61C 9/00* (2006.01)

(52) U.S. Cl.
CPC .......... *A61C 8/0001* (2013.01); *A61C 9/0006* (2013.01); *A61C 9/002* (2013.01)

(58) Field of Classification Search
CPC .................................................. A61C 8/0001
See application file for complete search history.

(56) References Cited

U.S. PATENT DOCUMENTS

| | | | |
|---|---|---|---|
| 5,904,483 A * | 5/1999 | Wade ................... | A61C 8/0048 433/173 |
| 6,213,773 B1 | 4/2001 | Gittleman | |
| 6,790,040 B2 | 9/2004 | Amber et al. | |
| 7,632,096 B2 | 12/2009 | Gittleman | |
| 7,654,824 B2 | 2/2010 | Ebi et al. | |
| 8,398,400 B2 | 3/2013 | Bondar | |
| 8,419,429 B2 | 4/2013 | Wang | |
| 8,632,336 B2 | 1/2014 | Rossler et al. | |
| 2007/0281278 A1 | 12/2007 | Jorneus et al. | |
| 2014/0227664 A1 | 8/2014 | Von Malottki | |
| 2017/0151038 A1 * | 6/2017 | Fan ..................... | A61C 8/0001 |

* cited by examiner

*Primary Examiner* — Ralph Lewis
(74) *Attorney, Agent, or Firm* — Lathrop Gage L.L.P.

(57) ABSTRACT

A low profile winged impression post having snap-in features eliminates the need for individual impressions of the mandibular and maxillary arches as well as a separate bite registration when registering a dental implant. The low profile impression post is retained by a press fit which eliminates the cumbersome task of screwing in the implant post. The time and steps needed to produce a stone model for construction are shortened. The same low profile impression post can be scanned optically for accurate placement in a virtual three dimensional space model of the jaw. A physical model can be generated in rigid polymer from the virtual scan data.

6 Claims, 5 Drawing Sheets

CIP FOR SCANNED AND EMBEDDED LOW PROFILE SNAP-IN WINGED DUAL USE DENTAL IMPRESSION POST

BACKGROUND OF THE INVENTION

In the field of dental implants, patient comfort and the efficient use of a dentist's time are paramount. Likewise, precision alignment of the prosthetic components is essential. The need to match upper and lower teeth to within a few microns and provide accurate mating of the prosthesis with existing teeth requires accurate replication of oral structures when making dental impressions. It is possible with the introduction of an intra-oral scanning apparatus to scan the oral environment and precisely display a working virtual model on a computer screen and to generate a physical model in accurate detail. Alternately, the more direct method of creating a physical stone model is still preferred by the majority of dentists.

To create accurate stone models for fitting the final prosthesis, a matched upper and lower impression can be obtained simultaneously with the jaw in the closed position and the teeth in the interdigitated position (centric occlusion). Currently, the tall impression transfer posts used to register the implants to the upper and lower jaws prevent the full closure of the mouth while making the simultaneous upper and lower scans and impressions. The present invention remedies this oversight for both virtual scanning and physical modeling.

Existing practice has been to perform the following procedures. After dental implants have healed into the underlying bone structures of the mandible or maxilla and the soft tissue has healed around a protective healing cap or healing screw, a full set of upper and lower impressions of the mouth are made using individual full or partial arch upper and lower trays. A separate bite registration elastomeric impression is also made in centric closure. Positive casts of the upper and lower impressions are poured, mounted on a dental articulator and aligned in centric occlusion by means of the separate elastomeric bite registration.

In more detail, the prior art performs the following steps to make an accurate impression, the healing caps are removed from one or more dental implant fixtures and standard length impression transfer posts are accurately placed with retaining screws on each implant fixture. An impression tray filled with a self-hardening elastomeric impression material is pressed over the region of the dental arch containing the impression transfer posts.

After a few minutes, the elastomeric impression material has set. The tray is gently removed from the mouth leaving the tall standard impression posts still attached to the implant fixtures. The screw retaining the standard impression transfer post is removed and the tall impression post is attached to an implant analog. The impression post and attached implant fixture analog is reinserted in the elastomeric compound. Taking care to seat the impression post accurately. The pratitioner or a dental lab casts a stone model embedding the implant analog. The implant fixture analog is thus fixed accurately within the stone model. The stone model serves as the platform to craft the prosthesis. The healing cap is replaced on the dental implant fixture in the mouth. Another impression of the mating jaw is taken by the same method. A third elastomeric cast is made of the teeth in centric closure to insure later alignment.

The stone models of the upper and lower mouth structure with dental implant analogs exactly aligned and retained are molded in hard plaster stone from the separate impressions. These models are separately placed upon a dental articulator to mimic the actual jaw motions. The separate upper and lower stone casts are aligned in centric closure with the elastomeric bite cast. The final prosthesis is built and tried in for a non-interfering, good fit. This prosthesis relies upon proper replacement of the tall standard impression post to insure the properly aligned position.

With the optical scanning apparatus, a virtual three dimensional image of the whole oral environment can be created in a minute or two. The virtual image file can be transmitted electronically to a lab and a physical model of the upper and lower jaw can be printed in rigid polymer with a three dimensional printer.

Applicants offer an impression post serving the needs of both the physical casting techniques and the virtual scanning methods.

Applicants, in order quickly to make an accurate, simultaneous impression of the upper and lower teeth in the correct alignment use a dual arch impression tray such as the Triple Tray™. This tray consists of a molded plastic or metal assembly with a handle connected to a set of confining dams and a thin open screen mesh. The mesh is oriented horizontally and is to be placed between the mating occlusal surfaces of the teeth while the jaw is in the closed or centric position. The mesh is thin enough to allow complete centric closure. The mesh is flexible and porous to trap and retain an elastomeric impression compound.

The buccal and lingual dams are molded to the mesh. A paste of quick-setting elastomer is placed on both sides of the mesh within the confines of the dams. The mouth is closed with the upper and lower teeth in the closed or centric position while embedded within the curing elastomer. In this manner, a matching set of aligned upper and lower impressions along with the proper bite registration are made simultaneously.

The elastomeric impression materials, such as polyvinylsiloxane or polyether, are dimensionally stable, but need adequate thickness and surface area in contact with the impression transfer post to ensure accurate positioning and replication of the implant within the models mounted upon an articulator. Currently, long tapered impression transfer posts are used, which have adequate surface area to accurately register the elastomeric impression to the dental implant analog, but interfere with the use of a dual arch impression tray by preventing closure.

In prior art Neal B. Gittleman U.S. Pat. No. 6,213,773 Reduced Height Dental Impression Post, and Neal B. Gittleman U.S. Pat. No. 7,632,096, with all reference made therein, a low profile wing impression post is taught. The impression post is of reduced height to allow complete closure to obtain a triple impression of the upper and lower dentition as well as the dental occlusion. This impression post is removably attached to an installed implant fixture and remains embedded within the triple impression compound, when the impression is removed from the mouth. The winged coronal top of the impression transfer post has sufficient volume and surface area to remain accurately fixed and stable within the impression compound. An implant fixture analog is mated with the impression transfer post and cast in the stone model. The prosthesis is accurately built upon implant fixture analog, with a matching manufactured abutment.

Features of the Invention

Prior art method for taking an impression and creating an accurate model of the dentition involve numerous steps. A number of these steps are eliminated with the methods and apparatus described herein.

The apparatus and method describes a preparation for a single implant. It is understood that one or more implants are served by the same technique.

After the post surgical healing and oseointegration of the implant in the bone, the following steps are required to create an accurate model using the prior art:
1. The healing cap is unscrewed from the implant fixture.
2. A full height standard impression post is set in position and screwed in place on the implant fixture.
3. An X-ray confirmation of the proper seating of the impression post.
4. A single full or half arch tray impression is taken of either the upper or lower dentition to index the impression post in relation to the surrounding dentition.
5. The single tray impression is removed leaving the impression post attached to the implant fixture.
6. The impression post is removed from the implant fixture and installed back into the impression tray.
7. The healing cap is replaced.
8. A bite impression is taken with polyvinyl elastomeric compound of the upper and lower dentition in centric closure.
9. An alginate impression of the opposing dentition is taken and a stone cast of the alginate is poured before dimensional shrinkage of the alginate through moisture evaporation.
10. The opposing stone cast, impression tray with installed impression post or posts, and bite impression are sent to the lab for stone model construction and the manufacture of the prosthesis.

In Neal B. Gittleman U.S. Pat. No. 7,632,096, with all reference made therein, a low profile impression cap shortens the steps and time needed to accomplish the same outcome.

The shortened number of steps needed are:
1. The healing cap is unscrewed from the surgically implanted implant fixture.
2. The low profile winged impression post is mated with the implant fixture.
3. A combined dual arch impression (e.g. Triple Tray™) is taken with the upper and lower dentition in centric closure. Upon removal, the triple tray and the impression material retain the low profile winged impression post.
4. An analog of the implant fixture is removably attached to the embedded impression post and a stone model is cast.
5. The healing cap is replaced in the implant fixture in the mouth and the dual arch impression is sent to the laboratory.

Embodiments of the invention have at least one positive locking member to mate and hold the low profile winged impression post in place on the implant fixture while the impression material is curing. The positive locking member releases from the implant fixture upon removal of the dual arch impression tray with the cured compound from the mouth.

A defining feature of the current application includes a flat surface situated preferably toward the buccal aspect of the low profile winged impression post with at least three points of reference to accurately locate and orient the low profile impression post by optical scanning means. The three points are visible to the scanner even while the teeth are in centric closure. Knowledge of the position of the three points defines a plane in known orientation to the central axis and depth of placement of the implant fixture. These at least three points on the impression post firmly locate the implant fixture in virtual space. The low profile impression post serves to locate the implant fixture in both virtual and physical space.

The low profile impression post three dimensional optical scan can be used to generate a physical model in rigid polymer from the virtual scan data.

DETAILED DESCRIPTION OF THE DRAWINGS

Figure 1:
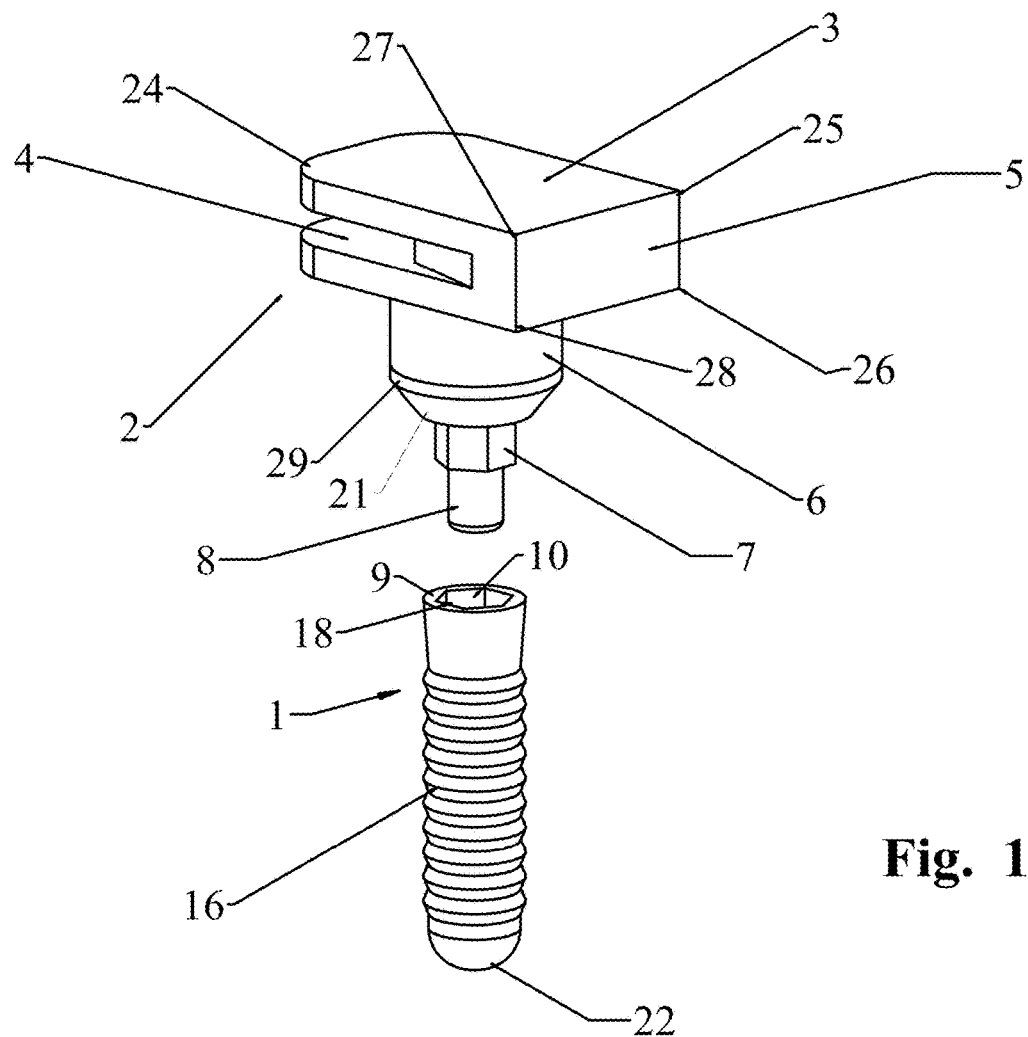
FIG. 1 is perspective view of a low profile winged impression post mated to an implant fixture.

FIG. 1 shows an implant fixture 1 having an apex 22 an outward circumferential thread 16, an upper surface 9 having a recess 10 with hexagonal clocking surfaces 18. An internal screw thread (not shown) is axially within the implant fixture. A cylindrical projection 8 of the dual use, low profile impression post 2 press fits and is removeably retained within the internal screw thread.

Clocking extension 7 fits within the recess 10. This clocking extension can be shaped to mate intimately with those implant families with different internal recesses having cross sections, such as hexagonal, octagonal, square, tapered fit, or lobed cross sections.

The low profile impression post 2 has a conical transition region 21 to cylindrical portion 6 having a circumferential metal ring. The circumferential metal ring 29 surrounds the cylindrical portion 6 to indicate the proper seating with no gap between the implant fixture and the impression post in a confirming X-ray image. The impression cap is removably mated and locked in the implant fixture. The upper or distal portion of the impression post has features to accommodate both physical impressions and virtual scans. Winged end 24 with gap 4 provides enough surface area to accurately be retained within the elastomeric compound. Coronal surface 3 does not extend into the bite plane. Surface 5 has at least three identifiable points for optical scanning. Four sharp corner points 25-28 are shown in FIG. 1. This surface faces to the buccal for easy optical scanning. These three or more accurately identifiable points form a plane having a known relationship to the cylindrical projection 8 and the clocking extension 7, thus defining the accurate position of the virtual implant fixture axis and depth in the bone.

Figure 2:
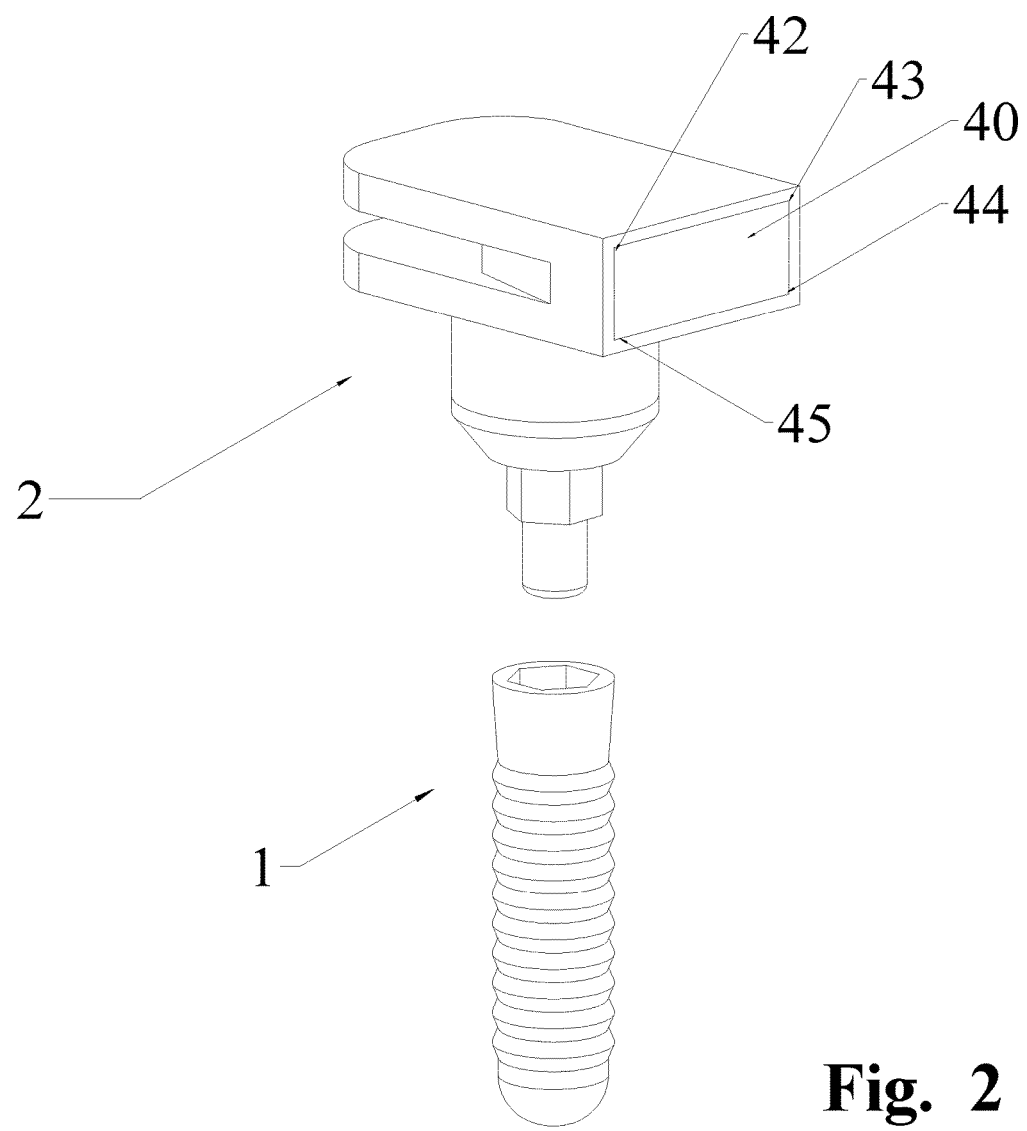
FIG. 2 is perspective view with embedded visibly contrasting tag.

FIG. 2 shows an optically non-reflective, optically distinctive, metal plate 40 embedded on the surface 5 having at least three identifiable points to define a plane in the scanned virtual space. The four corners 42-45 serve this purpose. Alternate shapes, notably a triangle having sharply defined points act to define this plane surface of the impression post. Alternately, as in FIG. 3, a two shot molding process could fill defined regions 52-55 on surface 5, the second shot having a contrasting color additive to locate at least three accurate points for optical scanning and alignment.

Figure 3:
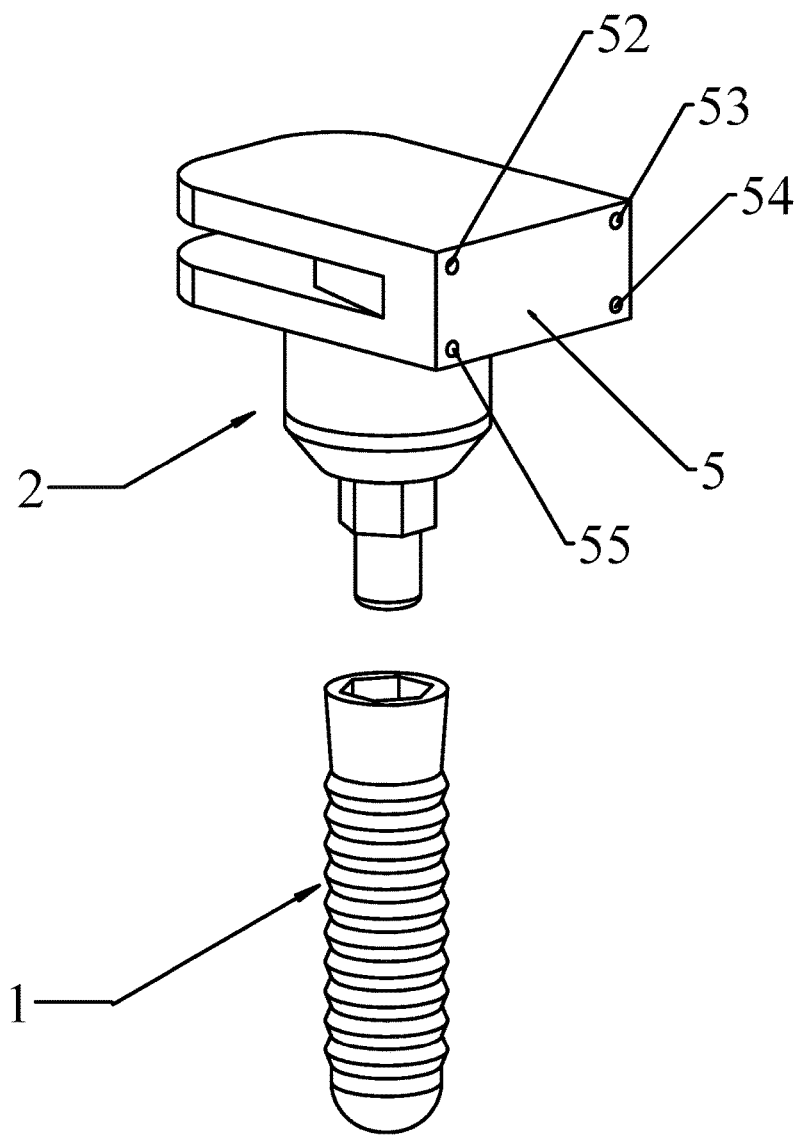
FIG. 3 is perspective view with visible spot markers.
Figure 4:
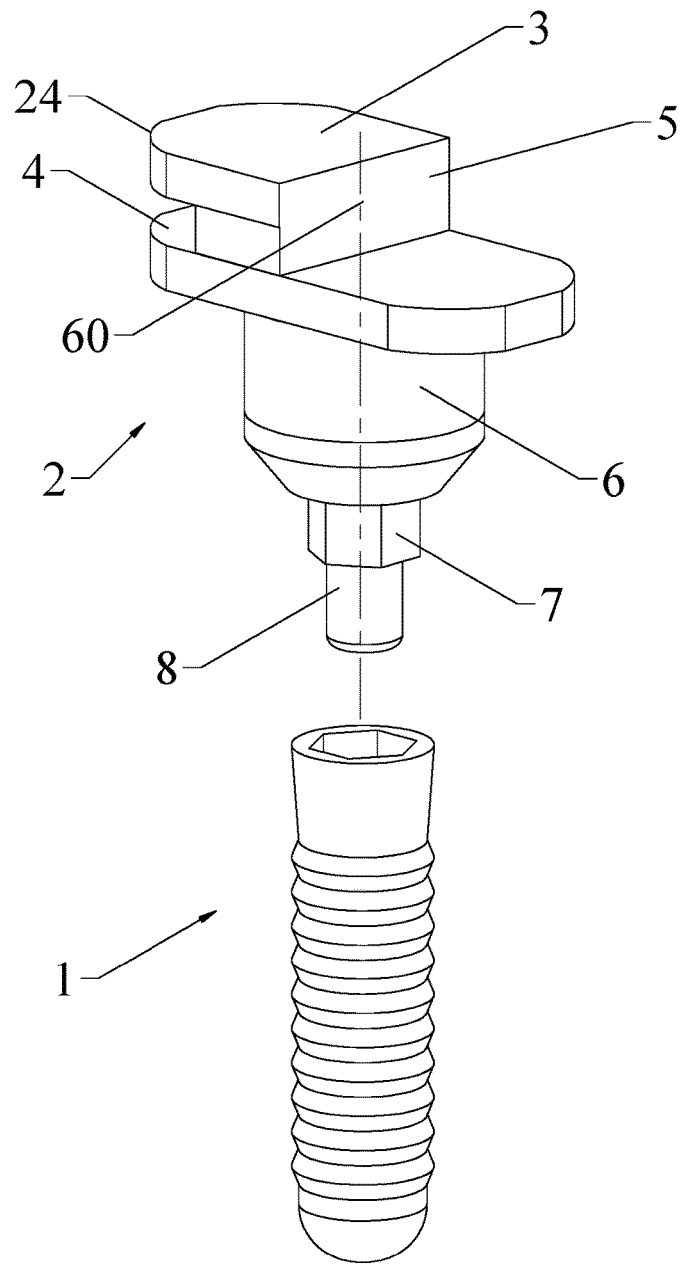
FIG. 4 is a perspective drawing of an impression post with an alternate scanning surface;
and,
FIG. 5 is a perspective drawing of an impression post with a single layer coronal region.

FIG. 4 details an alternate placement for the scanning surface 5 with at least two points lying upon the central axis 60 of the implant fixture. The scanning surface 5 has at least three distinctive points to define a plane precisely oriented with the implant fixture. Though not shown, FIG. 4 can incorporate a metal plate 40 as shown in FIG. 2 or a number of well defined regions 52-55 as shown in FIG. 3.

Though the cross section of clocked projection 7 is shown to be a hexagon, other clocking cross sections including but not limited to octagonal or square, lobed, tapered or cylindrical with a single or multiple flat faces.

Figure 5:
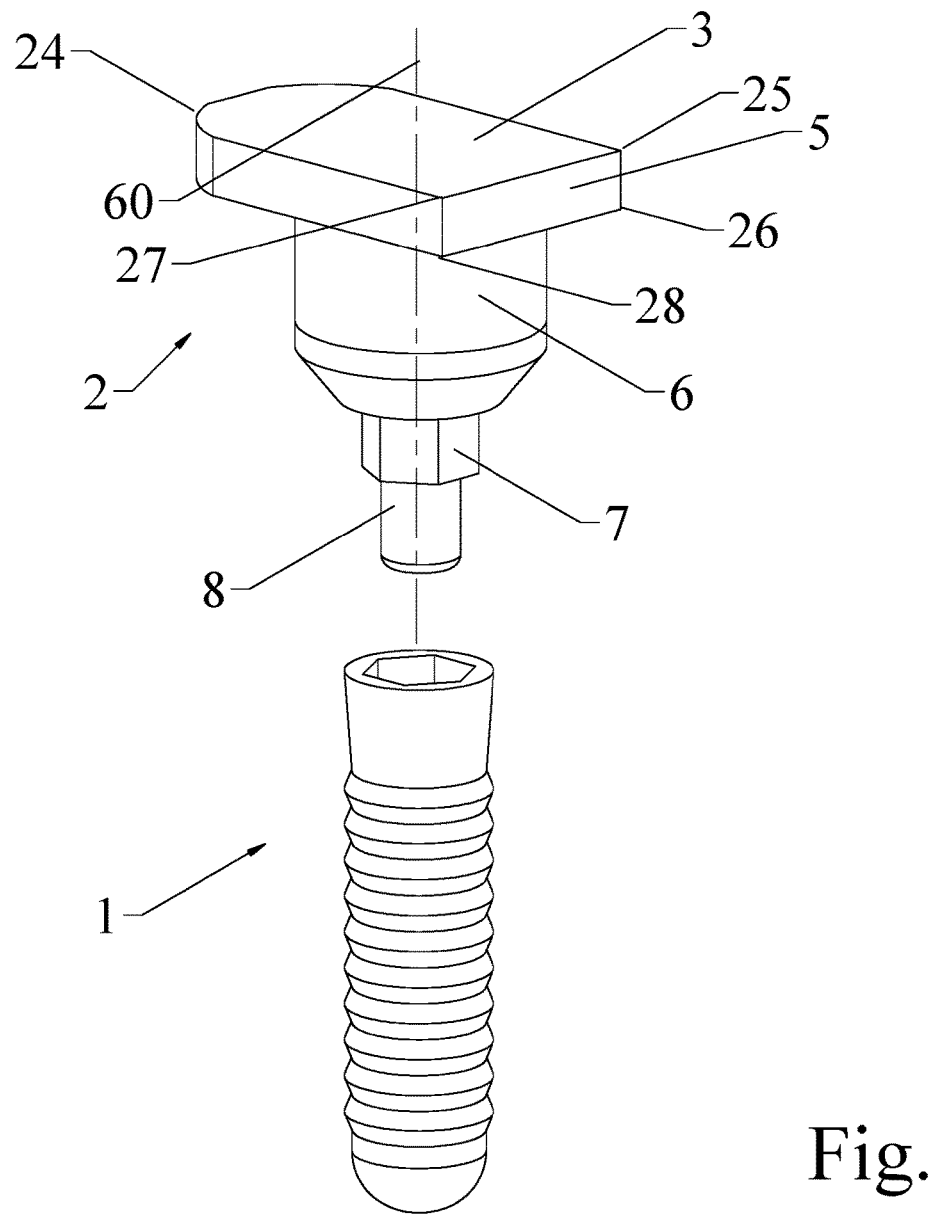

FIG. 5 is a single winged low profile impression post with a surface 5 having at least three distinctive points or corners 25-28 of reference for an accurate optical scan. This is useful in those circumstances where a shorter impression post is needed. It is understood that whatever form the coronal region of the low profile impression post takes, this region has adequate surface and volume to remain accurately fixed within the elastomeric compound and to have a definable surface with at least three distinctive points to accurately define the location of the attached implant fixture if the optical scanning method is used.

These embodiments of the invention include projections that reach into and latch within the internal screw threads of the implant fixture.

The low profile impression cap can be molded as one piece from suitable materials, such as nylon, PEEK, or other dimensionally stable polymers.

A two shot molding process can be used to form contrasting color regions or spots on the scanning surface to accurately define the axis and depth of the implant fixture. A laser marking apparatus can be used to form precise contrasting points on the scanning surface.

A number of suitable impression posts can be included in each implant fixture kit to anticipate any dental modeling situation.

What is claimed:

1. A dental apparatus comprising:
    an implant fixture having a prism recess of plural inwardly facing planar facets in an upper end thereof, an external circumferential screw thread proximate an apex end thereof, opposite the upper end, and an internal screw thread coaxial with the external circumferential screw thread; and
    a low profile winged impression transfer post having, comprising
        a top wing with a dimensionally stable scanning surface;
        a second wing to add retention;
        a connecting neck linking the top wing and the second wing;
        a cylindrical body attached to the second wing;
        a prism projection attached to the cylindrical body and configured for removable mating with the prism recess in the implant fixture; and
        a through hole extending through the top wing, second wing, connecting neck, cylindrical body and prism projection for accommodating a retention screw therein,
    wherein the prism projection has plural outwardly facing planar facets and at least one semi-spherical projection extending outwardly from at least one of the outwardly facing planar facets for pressing against and deforming in contact with a corresponding inwardly facing planar facet of the prism recess of the implant fixture to enable temporary firm attachment between the winged impression transfer post and the implant fixture.

2. The dental apparatus as described in claim 1, further comprising:
    a tapered recess in the upper end of the implant fixture proximate the prism recess; and
    a tapered projection extending between the cylindrical body and the prism projection of the winged impression transfer post to enable removable mating with the tapered recess in the implant fixture.

3. The dental apparatus as described in claim 1, wherein
    the prism projection has at least two outwardly facing planar facets each having at least one semi-spherical outwardly extending projection;
    the at least one semi-spherical projections configured for pressing against and deforming in contact with an inwardly facing planar facet of the prism recess of the implant fixture to enable temporary firm attachment between the winged impression transfer post and the implant fixture.

4. The dental apparatus as described in claim 1, wherein
    the prism projection has a triangular arrangement of semi-spherical projections extending outwardly from each of one or more of the outwardly facing planar facets for pressing against and deforming in contact with a corresponding inwardly facing planar facet of the prism recess of the implant fixture to enable temporary firm attachment between the winged impression transfer post and the implant fixture.

5. The dental apparatus as detailed in claim 4, wherein a semi-spherical projection first engaging the corresponding inwardly facing planar facet as the winged impression transfer post is inserted into the implant fixture extends outwardly less than a semi-spherical projection on the same outwardly facing planar facet later engaging the same corresponding inwardly facing planar facet to facilitate insertion of the prism projection of the winged impression transfer post into the prism recess of the implant fixture.

6. The dental apparatus as detailed in claim 1, further comprising
    a pilot pin comprising a head and a cylindrical body,
    wherein the cylindrical body is configured to firmly, removably fit within the through hole in the winced impression transfer post
    and into the implant fixture internal threads for a removable friction fit.

* * * * *